United States Patent
Henley et al.

(10) Patent No.: US 10,561,302 B2
(45) Date of Patent: Feb. 18, 2020

(54) VIEWING TROCAR WITH INTEGRATED PRISM FOR USE WITH ANGLED ENDOSCOPE

(71) Applicant: Depuy Synthes Products, Inc., Raynham, MA (US)

(72) Inventors: Jeremiah D. Henley, Midvale, UT (US); Joshua D. Talbert, Cottonwood Heights, UT (US); Brian Dean, Salt Lake City, UT (US); Perry W. Croll, Sandy, UT (US); Marshall Denton, Salt Lake City, UT (US); J. Michael Brown, Salt Lake City, UT (US)

(73) Assignee: DePuy Synthes Products, Inc., Raynham, MA (US)

( * ) Notice: Subject to any disclaimer, the term of this patent is extended or adjusted under 35 U.S.C. 154(b) by 425 days.

(21) Appl. No.: 14/214,400

(22) Filed: Mar. 14, 2014

(65) Prior Publication Data

US 2014/0275771 A1   Sep. 18, 2014

Related U.S. Application Data

(60) Provisional application No. 61/791,935, filed on Mar. 15, 2013.

(51) Int. Cl.
*A61B 1/00*   (2006.01)
*A61B 17/34*   (2006.01)
*A61B 1/313*   (2006.01)

(52) U.S. Cl.
CPC ...... *A61B 1/00096* (2013.01); *A61B 1/00135* (2013.01); *A61B 1/00154* (2013.01);
(Continued)

(58) Field of Classification Search
CPC . A61B 17/34; A61B 17/3415; A61B 17/3417; A61B 17/3421; A61B 17/3423; A61B 17/3431; A61B 17/3439; A61B 17/3462; A61B 17/347; A61B 17/3478; A61B 2017/3425; A61B 2017/3427;
(Continued)

(56) References Cited

U.S. PATENT DOCUMENTS

| 4,011,403 A | 3/1977 | Epstein et al. |
| 4,363,963 A | 12/1982 | Ando |

(Continued)

FOREIGN PATENT DOCUMENTS

| WO | 1996005693 A1 | 2/1996 |
| WO | 2008079373 A1 | 7/2008 |
| WO | 2012155142 A1 | 11/2012 |

*Primary Examiner* — Ryan N Henderson
(74) *Attorney, Agent, or Firm* — Terrence J. Edwards; TechLaw Ventures, PLLC (57) ABSTRACT

Endoscopic light refraction imaging techniques are described for configuring a viewing trocar and/or angled endoscope with a light refracting element, such as glass and/or plastic prism for instance. The light refracting element can be utilized in and/or with the viewing trocar to refract (i.e., bend) light passing into the trocar through the trocar's window. As a result, the angled endoscope's field of view can be substantially aligned with the field of view of the trocar's window, thus allowing the angled endoscope and viewing trocar to be used together to create ports in a patient, including initial ports of endoscopic surgical procedures.

8 Claims, 8 Drawing Sheets

(52) U.S. Cl.
CPC ........ *A61B 1/00179* (2013.01); *A61B 1/3132* (2013.01); *A61B 17/34* (2013.01); *A61B 17/3417* (2013.01); *A61B 17/3478* (2013.01)

(58) Field of Classification Search
CPC .... A61B 2017/3429; A61B 2017/3433; A61B 2017/3435; A61B 2017/3437; A61B 2017/3441; A61B 2017/3443; A61B 2017/3445; A61B 2017/3447; A61B 2017/3449; A61B 2017/345; A61B 2017/3452; A61B 2017/3454; A61B 2017/3456; A61B 2017/3458; A61B 1/05; A61B 1/051; A61B 1/00179; A61B 1/00181; A61B 1/00183
USPC ................ 600/104, 106, 121–125, 127, 129, 600/156–159, 170, 171, 175; 604/26, 604/43–45, 93.01, 164.01–164.11, 604/170.01–170.03, 506–510
See application file for complete search history.

(56) References Cited

U.S. PATENT DOCUMENTS

| | | | |
|---|---|---|---|
| 4,433,675 A | 2/1984 | Konoshima | |
| 4,740,837 A | 5/1988 | Yanagisawa et al. | |
| 4,741,327 A | 5/1988 | Yabe | |
| 4,745,471 A | 5/1988 | Takamura et al. | |
| 4,786,965 A | 11/1988 | Yabe | |
| 4,832,003 A | 5/1989 | Yabe | |
| 4,853,772 A | 8/1989 | Kikuchi | |
| 4,866,526 A | 9/1989 | Ams et al. | |
| 4,916,534 A * | 4/1990 | Takhashi | A61B 1/00096 348/337 |
| 4,918,521 A | 4/1990 | Yabe et al. | |
| 4,942,473 A | 7/1990 | Zeevi et al. | |
| RE33,584 E | 5/1991 | Mimura | |
| 5,016,975 A | 5/1991 | Sasaki et al. | |
| 5,021,888 A | 6/1991 | Kondou et al. | |
| 5,133,035 A | 7/1992 | Hicks | |
| 5,187,572 A | 2/1993 | Nakamura et al. | |
| 5,200,838 A | 4/1993 | Nudelman et al. | |
| 5,220,198 A | 6/1993 | Tsuji | |
| 5,228,430 A | 7/1993 | Sakamoto | |
| 5,241,170 A | 8/1993 | Field, Jr. et al. | |
| 5,313,306 A | 5/1994 | Kuban et al. | |
| 5,325,847 A | 7/1994 | Matsuno | |
| 5,385,572 A | 1/1995 | Nobles et al. | |
| 5,411,020 A | 5/1995 | Ito | |
| 5,427,087 A | 6/1995 | Ito et al. | |
| 5,454,366 A | 10/1995 | Ito et al. | |
| 5,551,947 A | 9/1996 | Kaali | |
| 5,554,097 A | 9/1996 | Guy | |
| 5,573,493 A * | 11/1996 | Sauer | A61B 1/00101 600/121 |
| 5,588,949 A | 12/1996 | Taylor et al. | |
| 5,594,497 A | 1/1997 | Ahern et al. | |
| 5,665,959 A | 9/1997 | Fossum et al. | |
| 5,718,664 A * | 2/1998 | Peck | A61B 1/00179 600/160 |
| 5,762,604 A | 6/1998 | Kieturakis | |
| 5,797,836 A * | 8/1998 | Lucey | A61B 1/00179 600/109 |
| 5,797,944 A | 8/1998 | Nobles et al. | |
| 5,817,061 A * | 10/1998 | Goodwin | A61B 17/3417 600/121 |
| 6,272,269 B1 | 8/2001 | Naum | |
| 6,310,642 B1 | 10/2001 | Adair et al. | |
| 6,327,493 B1 | 12/2001 | Ozawa et al. | |
| 6,331,156 B1 | 12/2001 | Haefele et al. | |
| 6,485,414 B1 | 11/2002 | Neuberger | |
| 6,508,759 B1 | 1/2003 | Taylor et al. | |
| 6,690,466 B2 | 2/2004 | Miller et al. | |
| 6,692,431 B2 | 2/2004 | Kazakevich | |
| 6,773,392 B2 | 8/2004 | Kikuchi et al. | |
| 6,809,358 B2 | 10/2004 | Hsieh et al. | |
| 6,895,270 B2 | 5/2005 | Ostrovsky | |
| 6,899,675 B2 | 5/2005 | Cline et al. | |
| 6,921,920 B2 | 7/2005 | Kazakevich | |
| 6,961,461 B2 | 11/2005 | MacKinnon et al. | |
| 7,037,259 B2 | 5/2006 | Hakamata et al. | |
| 7,189,226 B2 | 3/2007 | Auld et al. | |
| 7,258,663 B2 | 8/2007 | Doguchi et al. | |
| 7,261,687 B2 | 8/2007 | Yang | |
| 7,369,176 B2 | 5/2008 | Sonnenschein et al. | |
| 7,435,217 B2 | 10/2008 | Wiklof | |
| 7,540,645 B2 | 6/2009 | Kazakevich | |
| 7,544,163 B2 | 6/2009 | MacKinnon et al. | |
| 7,794,394 B2 | 9/2010 | Frangioni | |
| 7,801,584 B2 | 9/2010 | Iddan et al. | |
| 8,159,584 B2 | 4/2012 | Iwabuchi et al. | |
| 8,193,542 B2 | 6/2012 | Maehara | |
| 8,393,737 B2 | 3/2013 | Dassanayake et al. | |
| 8,698,887 B2 | 4/2014 | Makino et al. | |
| 8,836,834 B2 | 9/2014 | Hashimoto et al. | |
| 8,885,034 B2 | 11/2014 | Adair et al. | |
| 2001/0030744 A1 | 10/2001 | Chang | |
| 2003/0007087 A1 | 1/2003 | Hakamata et al. | |
| 2003/0189663 A1 | 10/2003 | Dolt et al. | |
| 2004/0082833 A1 | 4/2004 | Adair et al. | |
| 2005/0027164 A1 | 2/2005 | Barbato et al. | |
| 2005/0234302 A1 | 10/2005 | MacKinnon et al. | |
| 2005/0267328 A1 | 12/2005 | Blumzvig et al. | |
| 2005/0288546 A1 | 12/2005 | Sonnenschein et al. | |
| 2006/0069314 A1 | 3/2006 | Farr | |
| 2006/0173479 A1 * | 8/2006 | Smith | A61B 1/00135 606/185 |
| 2007/0129601 A1 | 6/2007 | Johnston et al. | |
| 2007/0244364 A1 | 10/2007 | Luanava et al. | |
| 2007/0244365 A1 | 10/2007 | Wiklof | |
| 2007/0276187 A1 | 11/2007 | Wiklof et al. | |
| 2008/0045800 A2 | 2/2008 | Farr | |
| 2008/0086074 A1 * | 4/2008 | Taylor | A61B 1/0008 604/26 |
| 2008/0108870 A1 | 5/2008 | Wiita et al. | |
| 2008/0165360 A1 | 7/2008 | Johnston | |
| 2008/0249369 A1 | 10/2008 | Seibel et al. | |
| 2009/0012361 A1 | 1/2009 | MacKinnon et al. | |
| 2009/0074265 A1 | 3/2009 | Huang et al. | |
| 2009/0154886 A1 | 6/2009 | Lewis et al. | |
| 2009/0160976 A1 | 6/2009 | Chen et al. | |
| 2009/0208143 A1 | 8/2009 | Yoon et al. | |
| 2009/0292168 A1 | 11/2009 | Farr | |
| 2009/0316116 A1 | 12/2009 | Melville et al. | |
| 2010/0016664 A1 * | 1/2010 | Viola | A61B 17/3423 600/114 |
| 2010/0121142 A1 | 5/2010 | OuYang et al. | |
| 2010/0290100 A1 | 11/2010 | Karasawa | |
| 2010/0305406 A1 | 12/2010 | Braun et al. | |
| 2011/0034795 A9 | 2/2011 | Gilad et al. | |
| 2011/0040253 A1 | 2/2011 | Sauer et al. | |
| 2011/0071349 A1 | 3/2011 | Drontle et al. | |
| 2011/0181840 A1 | 7/2011 | Cobb | |
| 2011/0199471 A1 * | 8/2011 | Tomioka | G02B 23/2423 348/65 |
| 2011/0237882 A1 | 9/2011 | Saito | |
| 2011/0237884 A1 | 9/2011 | Saito | |
| 2011/0288374 A1 | 11/2011 | Hadani et al. | |
| 2011/0319826 A1 * | 12/2011 | Zisow | A61B 17/3417 604/164.04 |
| 2012/0004508 A1 | 1/2012 | McDowall et al. | |
| 2012/0041267 A1 | 2/2012 | Benning et al. | |
| 2012/0041534 A1 | 2/2012 | Clerc et al. | |
| 2012/0050592 A1 | 3/2012 | Oguma | |
| 2012/0078052 A1 | 3/2012 | Cheng | |
| 2012/0140302 A1 | 6/2012 | Xie et al. | |
| 2012/0307030 A1 | 12/2012 | Blanquart | |
| 2013/0144122 A1 | 6/2013 | Adair et al. | |
| 2013/0158346 A1 | 6/2013 | Soper et al. | |
| 2014/0005532 A1 | 1/2014 | Choi et al. | |
| 2014/0052004 A1 | 2/2014 | D'Alfonso et al. | |
| 2014/0073852 A1 | 3/2014 | Banik et al. | |

(56) References Cited

U.S. PATENT DOCUMENTS

2014/0203084 A1 7/2014 Wang
2014/0316199 A1 10/2014 Kucklick
2014/0364689 A1 12/2014 Adair et al.

* cited by examiner

```
┌─────────────────────────────────────────────┐
│ Configure Viewing Trocar and Angled         │
│ Endoscope to be Operably Connected          │
│                    402                      │
└─────────────────────────────────────────────┘
                     │
                     ▼
┌─────────────────────────────────────────────┐
│ Configure Viewing Trocar or Angled          │
│ Endoscope with Light Refracting Element     │
│                    404                      │
└─────────────────────────────────────────────┘
                     │
                     ▼
┌─────────────────────────────────────────────┐
│ Configure Viewing Trocar with Retaining     │
│ Functionality                               │
│                    406                      │
└─────────────────────────────────────────────┘
```

VIEWING TROCAR WITH INTEGRATED PRISM FOR USE WITH ANGLED ENDOSCOPE

CROSS-REFERENCE TO RELATED APPLICATIONS

This application claims the benefit of U.S. Provisional Application No. 61/791,935, filed Mar. 15, 2013, which is hereby incorporated by reference herein in its entirety, including but not limited to those portions that specifically appear hereinafter, the incorporation by reference being made with the following exception: In the event that any portion of the above-referenced provisional application is inconsistent with this application, this application supersedes said above-referenced provisional application.

STATEMENT REGARDING FEDERALLY SPONSORED RESEARCH OR DEVELOPMENT

Not Applicable.

BACKGROUND

Advances in technology have led to numerous improvements in imaging capabilities for medical use. One area that has enjoyed some of the most beneficial advances is that of endoscopic surgical procedures. These procedures can be less invasive than traditional surgical procedures because they allow a patient's internal body portions, including the surgical site, to be examined (and sometimes treated) by inserting an imaging device called an endoscope into a small port in the patient.

Typically, to initiate an endoscopic procedure, a trocar is first utilized to create a small port, or pathway, to the surgical site of interest inside the patient. More particularly, the trocar is first inserted into a narrow endoscopic tube, or cannula. The trocar is then used to puncture the patient's tissue, distal portion first, to reach the surgical site. The trocar's distal portion typically terminates in a relatively sharp tip (i.e., insertion tip) to facilitate puncturing the tissue and reaching the surgical site. Once the surgical site is reached, the trocar can then be removed, leaving the cannula as the port.

When a trocar is used to puncture the patient's internal tissue, there is a risk that an organ or blood vessel may be accidentally ruptured. This is especially true when the initial port of a procedure is created because the trocar's first insertion into the patient cannot be viewed from inside the patient's body with an endoscope through another port.

To help mitigate this first-insertion risk, viewing trocars have been developed to allow the trocar's tip to be observed as it is inserted (i.e., punctures the patient) and passes through the patient's tissue to the surgical site. To accomplish this, viewing trocars are typically configured with a window at or near their distal portion and a hollow portion to allow an endoscope to be inserted. The endoscope can then be used to view the tip's insertion and passage through the patient's tissue through the window.

To provide a sufficient field of view to observe the tip, non-angled (zero-degree) endoscopes rather than angled endoscopes are typically used to create an initial port. Angled endoscopes, however, are commonly used and preferred for most other parts of many endoscopic procedures. This makes using a non-angled endoscope for such procedures inconvenient, costly, and inefficient, especially when the endoscope is a limited use, re-posable, or single-use/disposable endoscope.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where.

DETAILED DESCRIPTION

The disclosure extends to methods, devices, and systems for endoscopic light refraction imaging that allow angled endoscopes to be used with viewing trocars in a convenient, efficient, and less costly manner to create ports in a patient, including initial ports of endoscopic surgical procedures. In the following description of the disclosure, reference is made to the accompanying drawings, which form a part hereof, and in which is shown by way of illustration specific implementations in which the disclosure may be practiced.

It is understood that other implementations may be utilized and structural changes may be made without departing from the scope of the disclosure.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

Endoscopic light refraction imaging techniques are described that allow angled endoscopes to be used with viewing trocars in a convenient, efficient, and less costly manner to create ports in a patient, including initial ports of endoscopic surgical procedures.

In at least some implementations, a viewing trocar and/or angled endoscope of an endoscopic system can be configured with a light refracting element, such as glass and/or plastic prism for instance. The light refracting element can be utilized in and/or with the viewing trocar to refract (i.e., bend) light passing into the trocar through the trocar's window. More particularly, the light refracting element can change the incoming light's direction of travel to be along a plane substantially perpendicular to the endoscope's offset angle. As a result, the endoscope's field of view can be substantially aligned with the field of view of the viewing trocar's window.

In at least one implementation, the viewing trocar can be configured with a prism that is integrated with a lumen defined by the viewing trocar or that is removeably attached to the lumen. Alternatively or additionally, the angled endoscope can be configured with a prism that is integrated onto the endoscope or that is removeably attached to the endoscope.

In at least one implementation, the angled endoscope can be configured with an image sensor that is disposed at and/or near the endoscope's distal end or tip. The image sensor may be a digital charge-coupled device (CCD) and/or complementary metal-oxide-semiconductor (CMOS) array of active pixel sensors for example.

As noted above, endoscopic surgical procedures can be less invasive than traditional surgical procedures because they allow a patient's internal body portions (i.e., tissue) to be examined (e.g., observed, inspected, and/or diagnosed) and/or treated by inserting an endoscope into a small port in the patient.

For example, a surgeon can examine and/or treat a patient by inserting a type of endoscope known as a laparoscope through a port to reach the interior of the patient's abdominal or pelvic cavity. As another example, a surgeon might examine and/or treat a patient by inserting another type of endoscope known as an arthroscope through a port to reach the interior of the patient's joint, such as a knee joint.

Endoscopes are typically long slender objects with a light-gathering element (e.g., objective lens(es)) positioned at and/or near the endoscope's distal end, and an imaging system to receive optical images and convert them into electronic images that can be rendered on a display. The field of view of an endoscope's light gathering element may be referred to herein as the endoscope's field of view. The imaginary line passing through an endoscope from its distal end to the proximal end can generally define the endoscope's axis.

As will be appreciated and understood by those skilled in the art, the light gathering element of a non-angled endoscope is disposed substantially perpendicular to the axis such that the endoscope's field of view is not substantially offset relative to a plane extending transversely to the endoscope's axis (i.e., the transverse plane). As such, the distal end (i.e., the tip) does not define an angle relative to the transverse plane, and thus appears blunt.

The light gathering element of an angled endoscope, in contrast, is not disposed substantially perpendicular to its axis. Instead, the light gathering element and distal end define an angle relative to the transverse plane. The degree of this angle, which can be referred to as the endoscope's offset angle, can vary and may be between about 12 and about 90 degrees. However, endoscope offset angles of about 30 degrees (i.e., 30-degree endoscopes) and 45 degrees (i.e., 45-degree endoscopes) are commonly used for many endoscopic procedures. As a result, the angled endoscope's field of view is substantially offset relative to the transverse plane, and the distal end thus appears angled or pointed.

Most endoscopes are designed such that the image sensor of the endoscope's imaging device or sensor is positioned at or near the endoscope's proximal end. For example, the image sensor is typically positioned in the endoscope's hand-piece unit at and/or near the proximal end of the endoscope. In such a configuration, light can enter through the light gathering element at the endoscope's distal end and propagate along the endoscope's axis toward the image sensor. This image sensor can be configured to convert the optical image(s) represented by the light into an electronic signal that can then be used to render the image on a display. As a result, the endoscope needs to be configured with a complex set of precisely coupled optical propagation components for the light to propagate to the image sensor.

Since an endoscope's cost is typically dominated by its optics, optical propagation components can significantly increase the endoscope's cost (e.g., production cost). Additionally, optical propagation components can increase the endoscope's fragility since relatively minor impacts can easily damage these components or upset their relative alignments. This fragility necessitates frequent, expensive repair cycles in order to maintain image quality. Therefore, removing or decreasing the optical propagation components in an endoscope would be advantageous for at least the reason that it would reduce the endoscope's cost and fragility.

To this end, endoscopic imaging techniques are described herein that allow an endoscope to be configured with few or no optical propagation components, thus significantly decreasing the endoscope's cost and fragility as compared to traditional endoscopes. For example, in some implementations the endoscope can be configured with an image sensor positioned at and/or near the endoscope's distal end or tip rather than at and/or near the endoscope's proximal end or in the hand piece. As a result, the image sensor can be located comparatively closer to the endoscope's light gathering element, thus reducing or eliminating the need for optical propagation components in the endoscope.

Typically, to initiate an endoscopic surgical procedure, a trocar is first utilized to create a port to the site of interest (e.g., surgical site) inside the patient. To accomplish this, the trocar can include an obturator configured with a relatively sharp tip at or near the trocar's distal portion for puncturing the patient's tissue and reaching the site of interest. Before being used to puncture the tissue, the obturator can first be inserted into a narrow endoscopic tube outside of the patient's body. The trocar (with the obturator inside the cannula) can then be inserted (distal portion first) into the patient. Once the site of interest is reached, the trocar can then be removed, leaving the cannula as the port.

When a trocar is used to puncture a patient's internal tissue during an endoscopic procedure, there is a risk that a vital organ or blood vessel may be accidentally ruptured, thus complicating the procedure. The ability to utilize an endoscope inserted via a port to observe the trocar's insertion from inside the patient can significantly mitigate this risk. However, this is not possible when the initial port of a procedure is created, thus making the puncture for an initial port more risky than subsequent punctures.

To help mitigate this first-puncture risk, viewing trocars (e.g., optical trocars) have been developed. Viewing trocars are typically configured with a transparent or translucent window to allow the trocar's tip (e.g., obturator's tip) to be observed as it is inserted (i.e., punctures the patient) and passes through the patient's tissue. A viewing trocar's window is usually positioned at and/or near the trocar's distal end. Viewing trocars are also typically configured with a hollow portion, or lumen, so that an endoscope can be inserted into the trocar to observe the tip's insertion and passage.

As one example, some viewing trocars are configured with a transparent or translucent obturator tip and lumen along the trocar's length (from proximal end to distal end). An endoscope can thus be inserted (e.g., slid) into the trocar such that the endoscope's light-gathering element is at and/or near (e.g., adjacent) the window. Light rays from the patient's tissue and/or other objects within the window's field of view and endoscope's field of view can enter through the window, be gathered and focused by the light gathering element, and viewed via the endoscope's imaging system and display.

Non-angled endoscopes are typically preferred to angled endoscopes for creating an initial port. This is because, when placed into a viewing trocar, a non-angled endoscope's field of view is typically substantially aligned with the field of view of the viewing trocar's window. As a result, little if any of the trocar's window is obscured from the endoscope's light-gathering element, and most or all of the light entering the trocar's window can reach the endoscope's light-gathering element.

In contrast, when an angled endoscope is placed into a typical viewing trocar, the endoscope's field of view is not typically substantially aligned with the field of view of the viewing trocar's window. This is due to the angled endoscope's offset angle. Generally, the greater the offset angle, the greater the extent that the field of view and window are out of alignment. For this reason, it is not surprising that most if not all viewing trocars are configured for non-angled endoscopes rather than angled endoscopes.

Angled endoscopes, however, are generally used and preferred for most types of endoscopic procedures other than creating the initial port. However, obtaining and utilizing both types of endoscopes, namely an angled and non-angled endoscope, can be costly, inconvenient, and wasteful—especially given that the non-angled endoscope may only be needed for creating the initial port. Therefore, it would be more convenient, efficient, and less costly to be able to use one angled endoscope for an entire endoscopic surgical procedure.

To this end, endoscopic light refraction imaging techniques are described herein. By utilizing these techniques, viewing trocars and/or non-angled endoscopes can be configured to be used together when creating ports in a patient, including an initial port of a procedure. For example, in some implementations a light refracting element (e.g., prism) can be utilized in and/or with a viewing trocar to refract (i.e., bend) light passing into the trocar through its window. More particularly, the light refracting element can change the incoming light's direction of travel to be along a plane substantially perpendicular to the endoscope's offset angle. As a result, the endoscope's field of view can be substantially aligned with the field of view of the trocar's window.

In other words, the light refracting element can be utilized to increase the amount of light that reaches the light gathering element by bending incoming light at an angle such that the fields of view of the endoscope and window are similar or the same. For example, if a 30-degree endoscope is inserted into the viewing endoscope, a prism can be used that bends incoming light at about a 30 degree angle towards the endoscope's light gathering element.

Figure 1A:
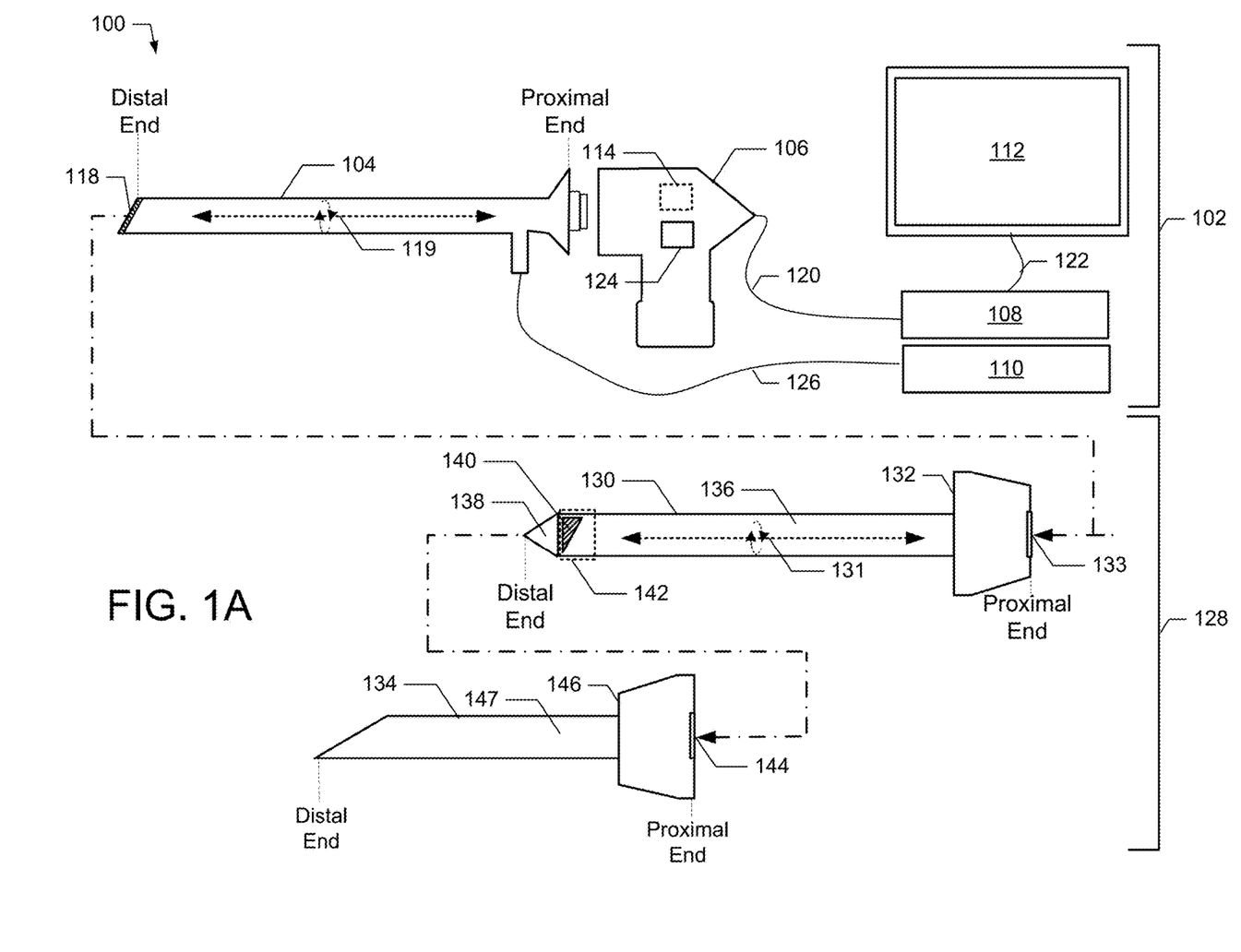
FIG. 1A illustrates an example endoscopic system according to at least one implementation and made in accordance with the teachings and principles of the disclosure.
Figure 1B:
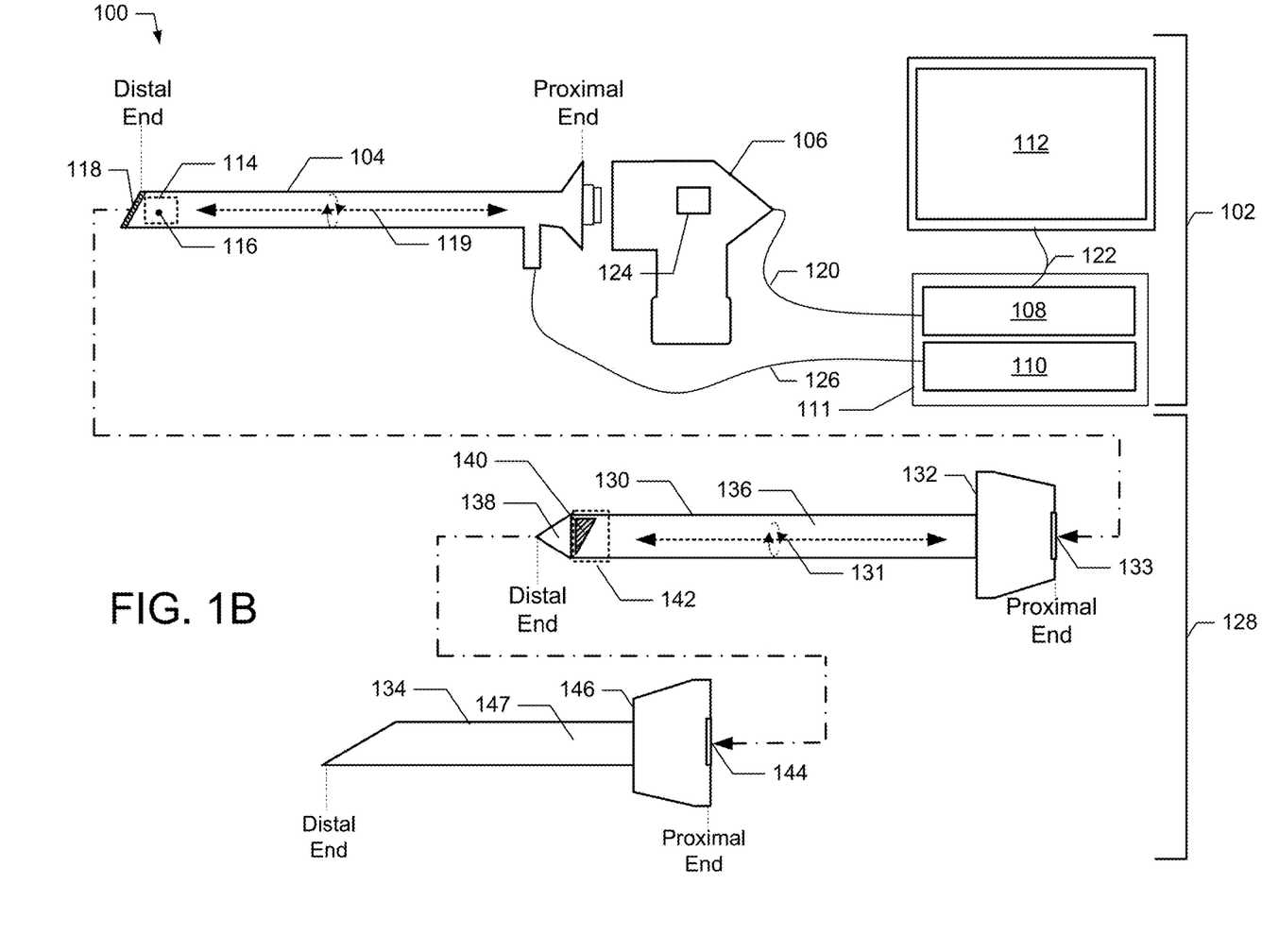
FIG. 1B illustrates an example endoscopic system according to at least one implementation and made in accordance with the teachings and principles of the disclosure.
Figure 1C:
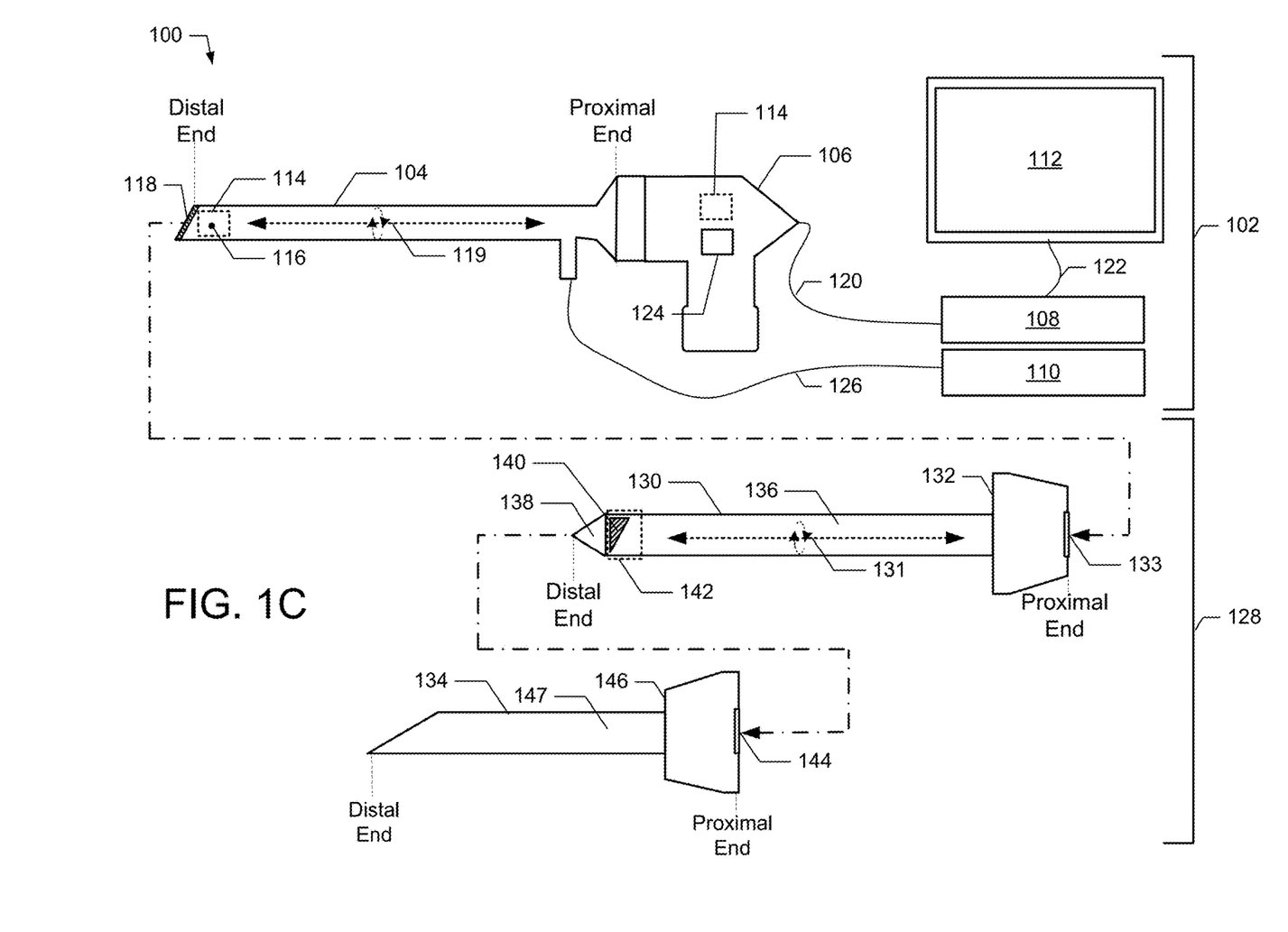
FIG. 1C illustrates an example endoscopic system according to at least one implementation and made in accordance with the teachings and principles of the disclosure.

To facilitate the reader's understanding of the disclosure, FIGS. 1A-1C illustrate exemplary endoscopic systems 100 that may be implemented in accordance with the techniques described herein. The endoscopic systems 100 illustrated are example implementations, and are thus not to be interpreted as limiting. More particularly, while the endoscopic systems 100 of FIGS. 1A-1C are described in the context of including various systems and components, this is not to be construed as limiting the implementation of any one or more of these systems or components to the endoscopic system 100. Instead, it is to be appreciated and understood that any of the described systems and components can be implemented alone or in any combination irrespective of the endoscopic system 100.

Referring to FIGS. 1A-1C, the endoscopic system 100 may include an angled endoscope system 102. The angled endoscope system 102, in turn, may include an endoscope device (i.e., endoscope) 104, endoscope housing 106 (e.g., hand piece and/or camera head), control unit 108, light source 110, display 112, and imaging device 114 (e.g., camera, sensors, etc.). Note that in this example, to facilitate discussion, the endoscope device 104, endoscope housing 106, control unit 108, light source 110, display 112, and imaging device 114 are each shown individually with respect to one another. However, it is to be appreciated and understood that this is not to be interpreted as limiting, and any one or more of these components can be integrated and/or connected in any suitable way.

For example, in FIGS. 1A and 1B the endoscopic device 104 and endoscope housing 106 are shown in a detached state. However, these components may be operably connected (e.g., coupled), as illustrated for example in FIG. 1C, to one another to form an angled endo scope unit for performing endoscopic surgical procedures.

As another example, in the implementation of FIGS. 1A and 1C, the control unit 108 and light source 110 are shown as being separate. Whereas, in the implementation of FIG. 1B, the control unit 108 and the light source 110 are shown as being part of the same unit 111. In either implementation, the light source 110 can be configured to provide light, when needed, via one or more fiber optics or other light transmission functionality to the endoscope device 104 for use in illuminating or otherwise facilitating observation of a patient's tissue. However, in some implementations (illustrated best in FIG. 1B) these components may be integrated (e.g., in the same housing, etc.) or otherwise operably connected in unit 111.

As yet another example, the imaging device 114 of FIG. 1C is shown as being configured with components located in both the endoscope housing 106 and endoscope device 104. However, in some other implementations the imaging device 114 may be configured otherwise. For example, in at least one implementation all of the features of the imaging device 114 can be included or located in the endoscope housing 106 (illustrated best in FIG. 1A), or alternatively some or all of the imaging device 114 can be located remotely or externally with respect to the endoscope housing 106 in one or more other components that may or may not include the control unit 108 or endoscope device 104.

In the example illustrated in FIG. 1B, the imaging device 114 includes an image sensor 116 that is advantageously disposed (i.e., located) at and/or near the distal end (i.e., tip) of the endoscope device 104. The image sensor 116 can be any suitable type of device and/or related circuitry, such as a digital charge-coupled device (CCD) and/or complementary metal-oxide-semiconductor (CMOS) array of active pixel sensors for instance.

In at least one implementation, to avoid or mitigate the image sensor 116 at the endoscope device's tip changing orientation and various display problems when a user rotates or changes the angle of the endoscopic device 104, certain mechanical and software stabilization techniques can be employed.

Operationally, the image sensor 116 can be configured to receive light gathered and focused by a light gathering element 118 (e.g., lens) positioned at and/or near the distal end of the endoscope device 104. The image sensor 116 can also be configured to convert optical images represented by the received light into electronic images that can be rendered on the display 112.

Note that in this example, the light gathering element 118 is not disposed substantially perpendicular to the axis 119 of the endoscope device 104. Instead, the light gathering element 118 is disposed at an angle of about 30 degrees relative to a plane extending transversely to the axis 119 (i.e., the transverse plane). Therefore the offset angle of the endoscope device 104 is about 30 degrees, thus making in the endoscope device 104 an angled endoscope. As a result of this offset angle, the field of view of endoscope device 104 is substantially offset relative to the transverse plane, thus resulting in the angled, or pointed, appearance of the distal end of the endo scope device 104.

Continuing, in operation, to facilitate electronic images being rendered on the display 112, the control unit 108 can be electronically and/or communicatively linked to the imaging device 114 and/or one or other components in the endoscope housing 106 and/or endoscope device 104. The control unit 108 can be linked in this manner via a physical (e.g., wired) and/or wireless (e.g., BLUETOOTH, infrared, etc.) connection, as represented by connection 120. Additionally, the control unit 108 can be electronically and/or communicatively linked to the display 112, as represented by connection 122. The display 112 may be any type of display device suitably configured to display rendered electronic images received from the imaging device 114.

In addition to including components of the imaging device 114, the endoscope housing 106 may also include other components, such as a transceiver 124 (e.g., wireless transceiver) that can be configured to facilitate communication between the endoscope housing 106 and the control unit 108 via the connection 120. The ability to separate and communicatively link the endoscope housing 106 from the control unit 108 (e.g., via wireless transmissions) may provide for the easy replacement of used endoscopes and/or endoscope housings for sterilized and renewed endoscopes and/or housings. The ability to separate and communicatively link these components also allows for greater mobility of the endoscope housing 106 during the endoscope device's use.

In addition to the endoscopic system 102, endoscopic system 100 may also include a viewing trocar system 128 that be configured to mitigate puncture risk during an endoscopic surgical procedure by allowing the distal end (i.e., tip) of the trocar system 128 to be observed as it is inserted into a patient and passes through the patient's tissue. More particularly, in this example the viewing trocar system 128 can include an obturator 130 and a cannula 134. The obturator 130 can include obturator housing 132, which in this example is shaped to facilitate handling of the obturator 130.

The obturator 130 can also define an interior obturator lumen 136 that extends along the axis 131 of the obturator 130 from the obturator's proximal end (at the obturator housing's proximal end) to a point at or near the relatively sharp tip at the obturator's distal end (i.e., trocar system's 128 distal end) that is formed by a transparent or translucent window 138.

In this example, the obturator housing 132 includes a hollow portion (e.g., trocar housing lumen) that effectively allows the obturator lumen 136 to extend from at or near the window 138 through the obturator housing 132 to an opening 133 at the housing's obturator's proximal end.

As will be appreciated and understood by those skilled in the art, the angled endoscope system 102 and viewing trocar system 128 can be configured to be operably connected (e.g., coupled) to one another to initiate an endoscopic surgical procedure. For example, the endoscope device 104 may be coupled with (e.g., slid into, and removed from) the obturator 130 by first inserting the endoscope device 104 (distal end first) through the opening 133 in the obturator housing 132 and along the obturator lumen 136 until the distal end of the endoscope device 104 reaches a point at or near the proximal end of the window 138.

Figure 2:
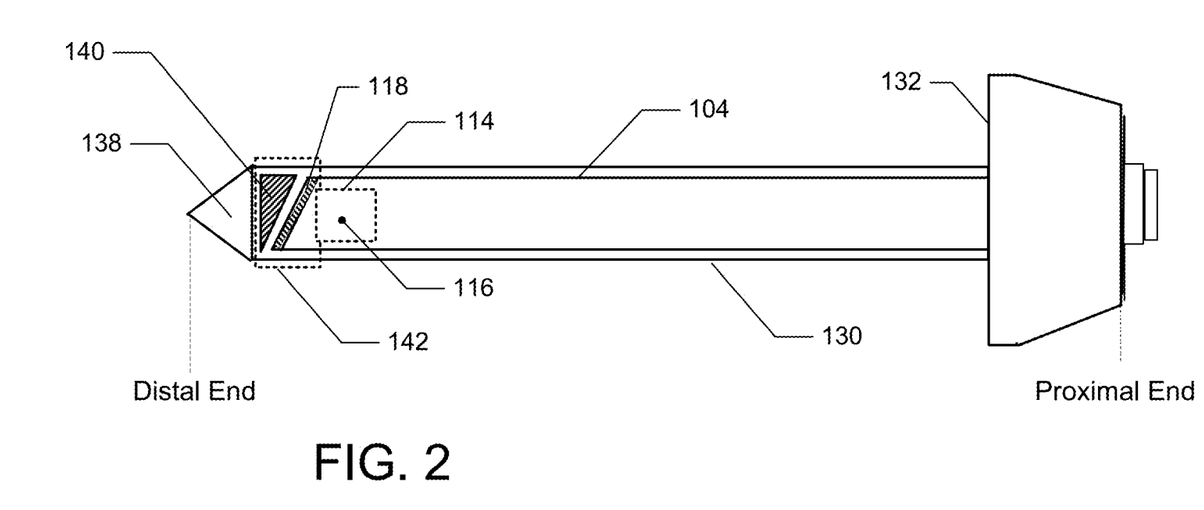
FIG. 2 illustrates an example of a connected angled endoscope device and viewing trocar according to at least one implementation and made in accordance with the teachings and principles of the disclosure.
Figure 3:
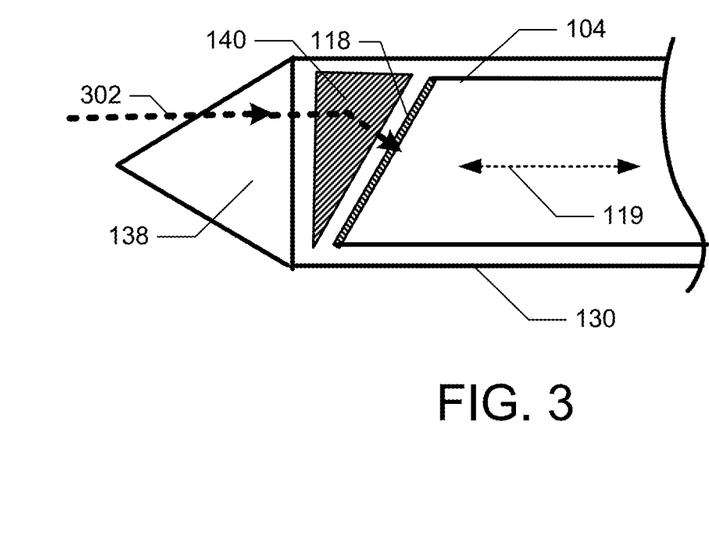
FIG. 3 is an enlarged, detailed view of a distal portion of an example connected angled endoscope device and viewing trocar according to at least one implementation and made in accordance with the teachings and principles of the disclosure.

Once the angled endoscope system 102 and viewing trocar system 128 are operably connected, as shown in FIG. 2, the light gathering element 118 and imaging device 114 (including image sensor 116) can be used to examine the tip formed by the window 138 as it is inserted into the patient's tissue. More particularly, in accordance with the described techniques, and as shown in FIGS. 2 and 3, when the angled endoscope system 102 and viewing trocar system 128 are operably connected a light refracting element 140 can be utilized in the obturator to bend incoming light 302 that has entered through the window 138. The light refracting element 140 can be any suitable type of device or material capable of refracting light in a particular direction. For example, in at least one implementation the light refracting element 140 is a prism made of glass and/or plastic that is able to cause the incoming light 302 to be bent toward the light gathering element 118. It will be appreciated that the light refracting element 140 may be made from any suitable material that has the ability to refract light as disclosed herein.

More particularly, the light refracting element 140 can be located in a light refracting region 142 in the obturator lumen 136 and disposed at an angle such that incoming light 302 is bent by the light refracting element 140 at a 30 degree angle in a direction toward the light gathering element 118, which is disposed at an angle of about 30 degrees relative to the transverse plane.

As illustrated in FIG. 3, the incoming light 302 can be bent by the light refracting element 140 such that the light's direction of travel is changed to be toward the light gathering element 118 along a plane that is substantially perpendicular to the light gathering element 118. As a result, the field of view of the endoscope device 104 can be substantially aligned with the field of view of the window 138, thus allowing the endoscope device 104 to be used in the viewing trocar system 128 in a convenient, effective, and cost efficient manner.

In some implementations, the light refracting element 140 can be integrated with the inside wall of the obturator lumen 136 and/or on the endoscope device 104, such that the element's location and/or position is fixed. Alternatively or additionally, the light refracting element can be placed into, and/or attached (i.e., temporarily or permanently) to, the obturator lumen 136 and/or to the endoscope device 104.

For example, in at least one implementation retaining functionality and structure can be utilized to place and/or attach the light refracting element 140 in a particular location and/or position in or on the obturator 130. The retaining functionality and structure may be configured to allow the light refracting element 140 to be removeably attached (e.g., temporarily) or permanently attached. For example, the retaining functionality and structure might be a mechanical structure, structurally integrated shape in the lumen or elsewhere in/on the obturator 130, adhesive chemical substance, and/or a region (e.g., the light refracting region 142) that allows the light refracting element 140 to be placed into, and/or attached to, the obturator 130.

Furthermore, in at least one implementation the retaining functionality and/or retention structures might be configured such that the light refracting element 140 remains fixed with the respect to the obturator lumen 136. In such an implementation, when coupled with the viewing trocar system, the endoscope device 104 would likely need to be rotated around the axis 131 (and thus axis 119) relative to the obturator 130 to reach a suitable orientation for the light refracting element 140 and light gathering element 118 to be substantially rotationally aligned, and thus adjacent to one another.

Alternatively, in at least one other implementation the retaining functionality may be configured such that the light refracting element 140 is allowed to move within the obturator lumen 136. In such an implementation, the endoscope device 104 may not need to be rotated around the axis 131 for the light refracting element 142 and light gathering element 118 to be substantially rotationally aligned, and thus adjacent to one another. Instead, the light refracting element 140 may be rotated around the axis 131 until alignment is achieved.

The retaining functionality and/or retention structures can also be configured to allow the light refracting element 140 to be manually and/or automatically disposed at one or more desired angles relative to a plane extending transversely to the axis 131 and/or to the endoscope device 104. For example, the retaining functionality and structure may be configured to allow the light refracting element's disposition to be changed from one desired angle to another desired angle.

The retaining functionality and/or light refracting element 140 can be provided in any suitable manner. For example, the retaining functionality and/or light refracting element 140 may be provided (e.g., commercially packaged) alone and/or with one or other components, such as with the viewing trocar system 128, endoscope device, and/or endoscopic system 100 for instance.

Finally, as will be appreciated and understood by those skilled in the art, the obturator 130 and trocar housing 132 may be operably connected to the cannula 134 before being inserted into the patient. As explained above, once the site of interest inside the patient is reached, the obturator 130 and/or trocar housing 132 can be removed, leaving the cannula as a port into the patient. In at least one implementation, the obturator 130 can be configured to be slid into, and removed from, the cannula 134 by first inserting the obturator 130 through an opening 144 in the cannula 134 and then along a cannula lumen 147 inside the cannula 134 until the distal end of the obturator housing 132 comes into contact with the proximal end of the cannula's housing 146.

To assist the reader in understanding the endoscopic light refraction imaging techniques described herein, an example method of configuring a viewing trocar and/or angled endoscope to be used together for an endoscopic procedure is described below.

Figure 4:
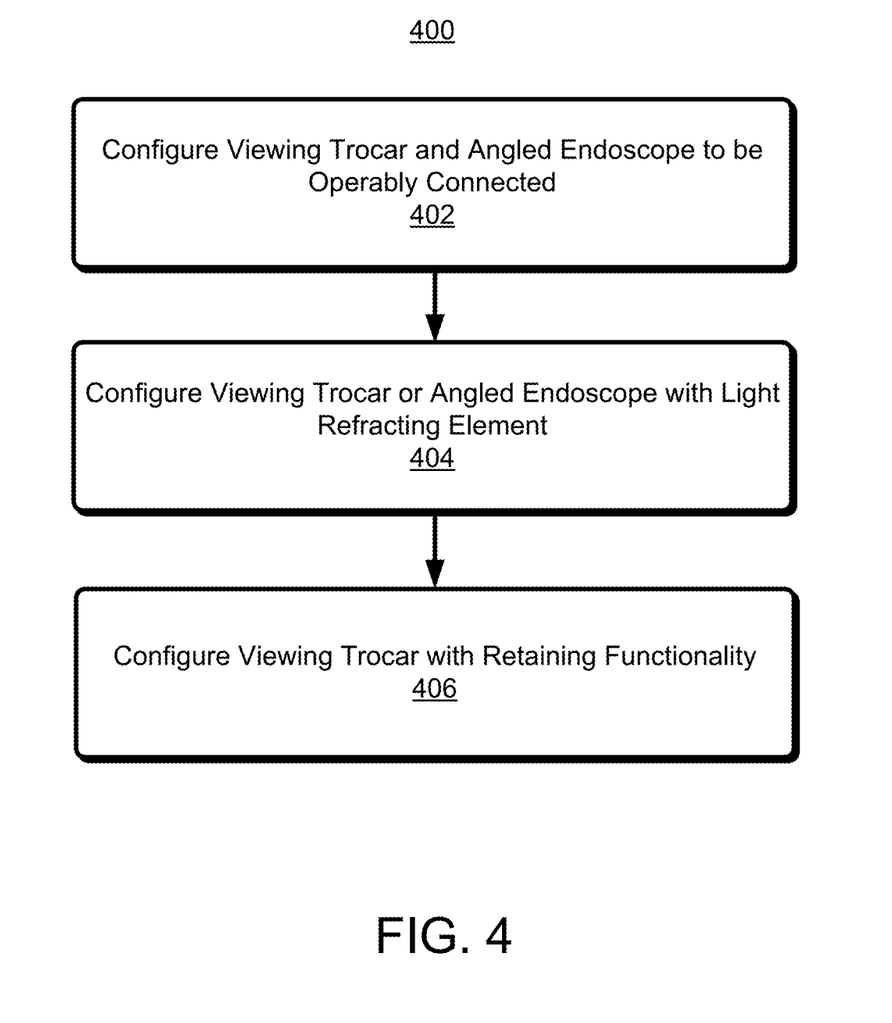
FIG. 4 illustrates an example method according to at least one implementation in accordance with the teachings and principles of the disclosure.

Regarding the method 400 illustrated in FIG. 4, at block 402 a viewing trocar and angled endoscope can be configured to be operably connected to place an endoscopic port. In at least one implementation, the viewing trocar system 128 and angled endoscope system 102 of endoscopic system 100 can be utilized.

At block 404 the viewing trocar or angled endoscope can be configured with a light refracting element (e.g., light refracting element 140), such a glass and/or plastic prism, to refract received light. As explained above, this light can be received through a window (e.g., window 138) disposed at the distal end of the viewing trocar. In at least one embodiment, the viewing trocar can be configured with a prism at or near the distal tip of the trocar that is integrated with a lumen defined by the viewing trocar, or that is removeably attached to the lumen. Alternatively or additionally, the angled endoscope can be configured with a prism that is integrated onto the endoscope or that is removeably attached to the endoscope.

Alternatively or additionally, at block 406 the viewing trocar can be configured with retaining functionality. As explained above, this retaining functionality and structure can be any functionality that allows the light refracting element to be placed into, and/or attached to, the viewing trocar.

It will be appreciated that the disclosure may be used with any image sensor, whether a CMOS image sensor or CCD image sensor, without departing from the scope of the disclosure. Further, the image sensor may be located in any location within the overall system, including, but not limited to, the tip of the endoscope, the hand piece of the imaging device or camera, the control unit, or any other location within the system without departing from the scope of the disclosure.

Implementations of an image sensor that may be utilized by the disclosure include, but are not limited to, the following, which are merely examples of various types of sensors that may be utilized by the disclosure.

Figure 5A:
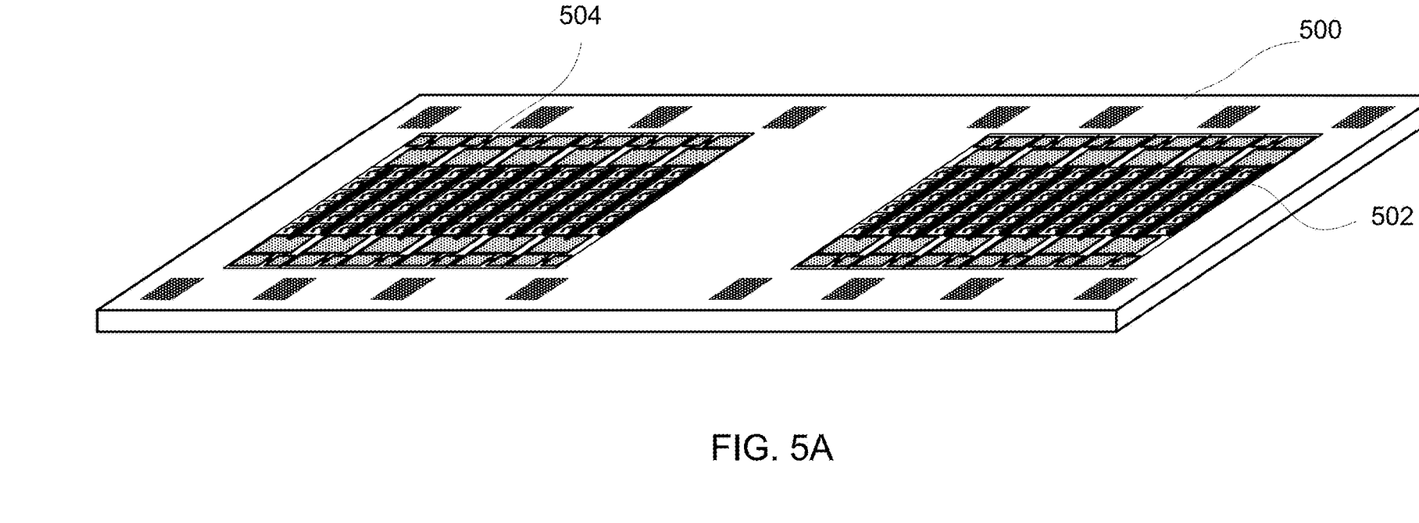
FIGS. 5A and 5B illustrate a perspective view and a side view, respectively, of an implementation of a monolithic sensor having a plurality of pixel arrays for producing a three dimensional image in accordance with the teachings and principles of the disclosure.
Figure 5B:
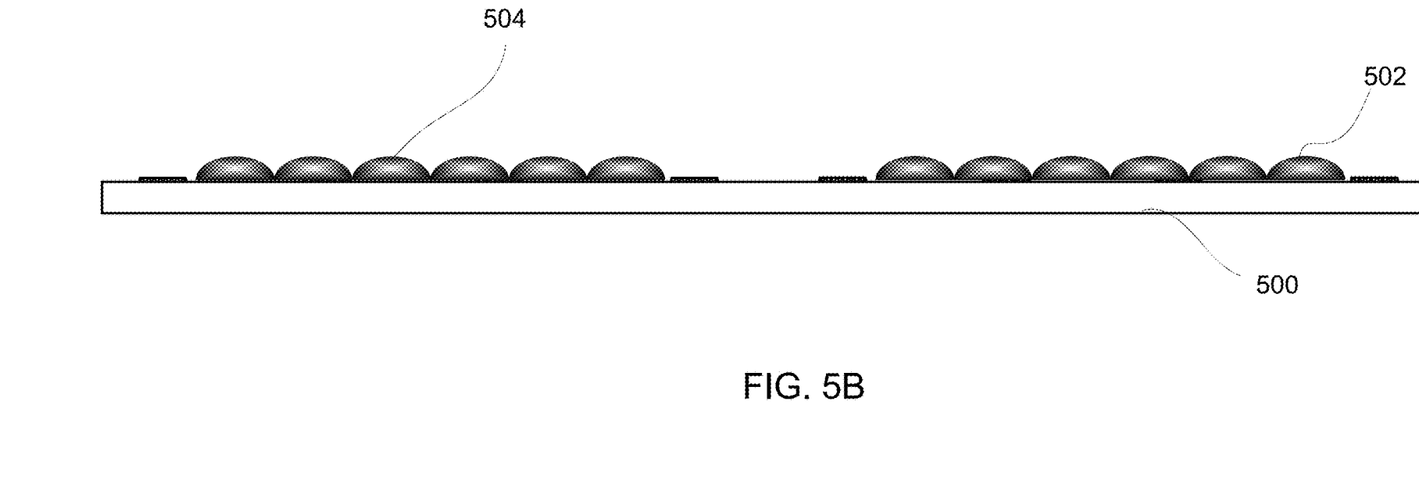

Referring now to FIGS. 5A and 5B, the figures illustrate a perspective view and a side view, respectively, of an implementation of a monolithic sensor 500 having a plurality of pixel arrays for producing a three dimensional image in accordance with the teachings and principles of the disclosure. Such an implementation may be desirable for three dimensional image capture, wherein the two pixel arrays 502 and 504 may be offset during use. In another implementation, a first pixel array 502 and a second pixel array 504 may be dedicated to receiving a predetermined range of wave lengths of electromagnetic radiation, wherein the first pixel array 502 is dedicated to a different range of wave length electromagnetic radiation than the second pixel array 504.

Figure 6A:
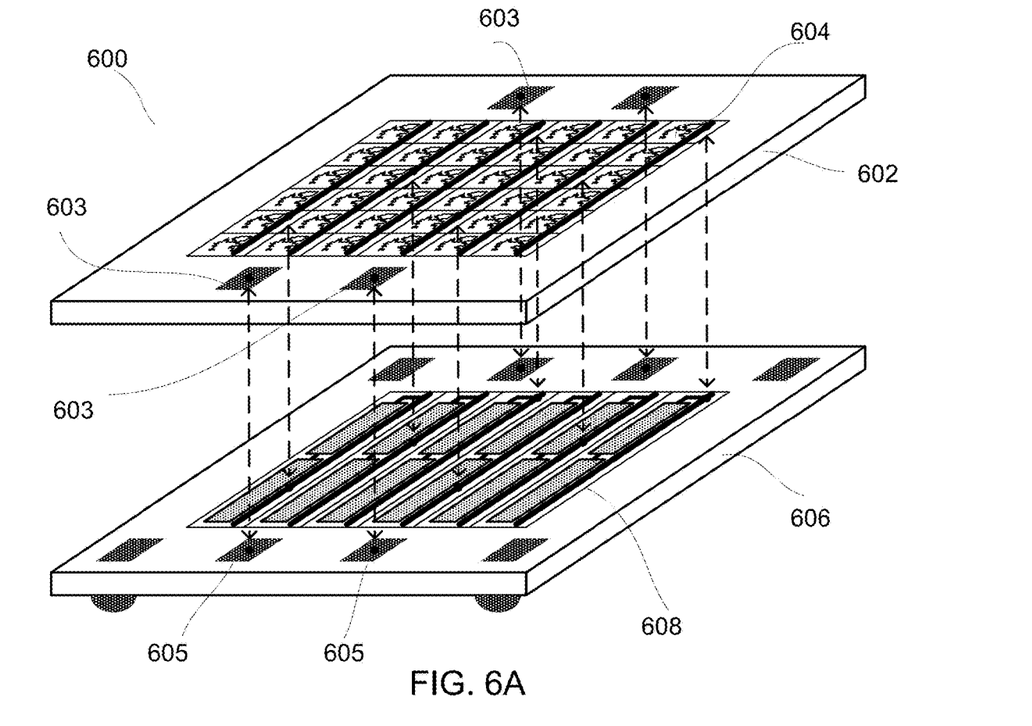
FIGS. 6A and 6B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 6B:
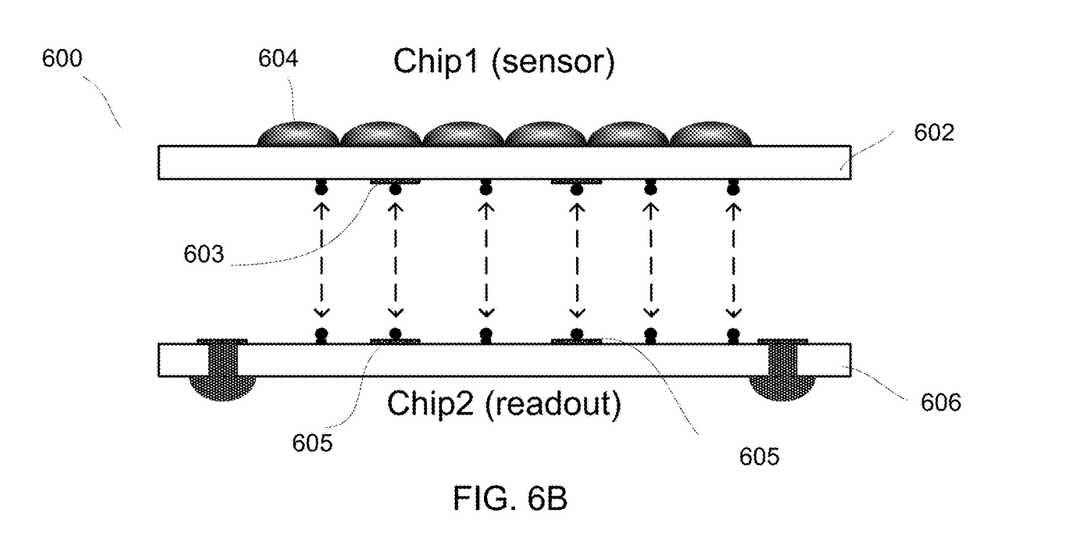

FIGS. 6A and 6B illustrate a perspective view and a side view, respectively, of an implementation of an imaging sensor 600 built on a plurality of substrates. As illustrated, a plurality of pixel columns 604 forming the pixel array are located on the first substrate 602 and a plurality of circuit columns 608 are located on a second substrate 606. Also illustrated in the figures are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 602 of the two substrates/chips may be processed using an image CMOS process. The first substrate/chip 602 may be comprised either of a pixel array exclusively or a pixel array surrounded by limited circuitry. The second or subsequent substrate/chip 606 may be processed using any process, and does not have to be from an image CMOS process. The second substrate/chip 606 may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip 602 may be stacked with the second or subsequent substrate/chip 606 using any three-dimensional technique. The second substrate/chip 606 may support most, or a majority, of the circuitry that would have otherwise been implemented in the first image CMOS chip 602 (if implemented on a monolithic substrate/chip) as peripheral circuits and therefore have increased the overall system area while keeping the pixel array size constant and optimized to the fullest extent possible. The electrical connection between the two substrates/chips may be done through interconnects 603 and 605, which may be wirebonds, bump and/or TSV (Through Silicon Via).

Figure 7A:
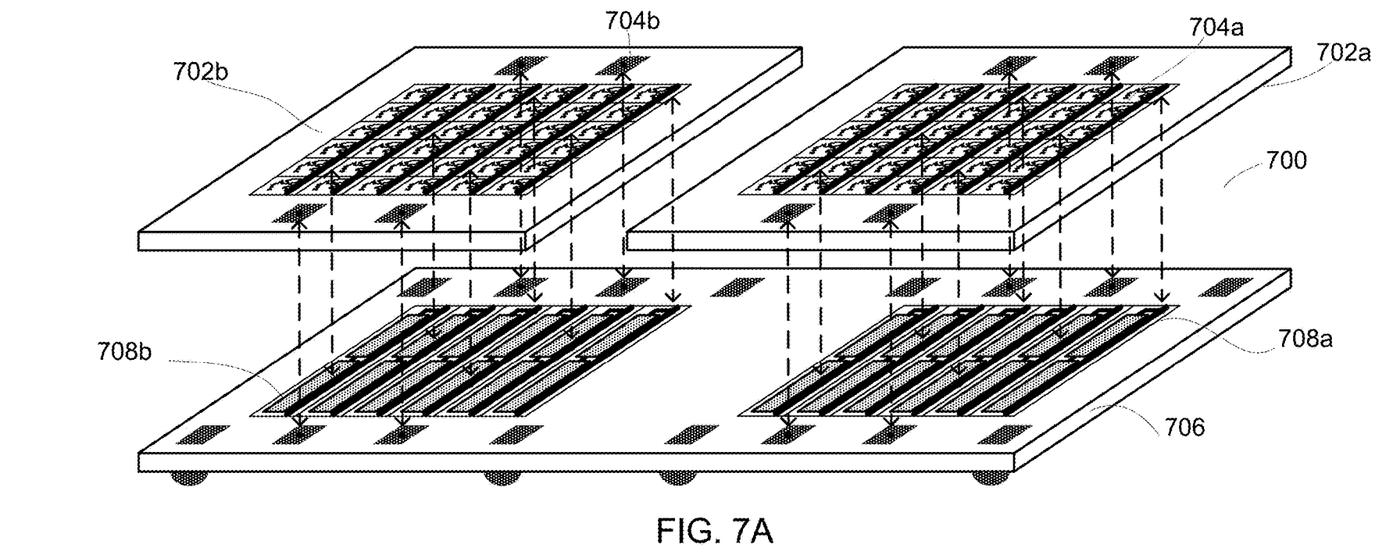
FIGS. 7A and 7B illustrate a perspective view and a side view, respectively, of an implementation of an imaging sensor having a plurality of pixel arrays for producing a three dimensional image, wherein the plurality of pixel arrays and the image sensor are built on a plurality of substrates.
Figure 7B:
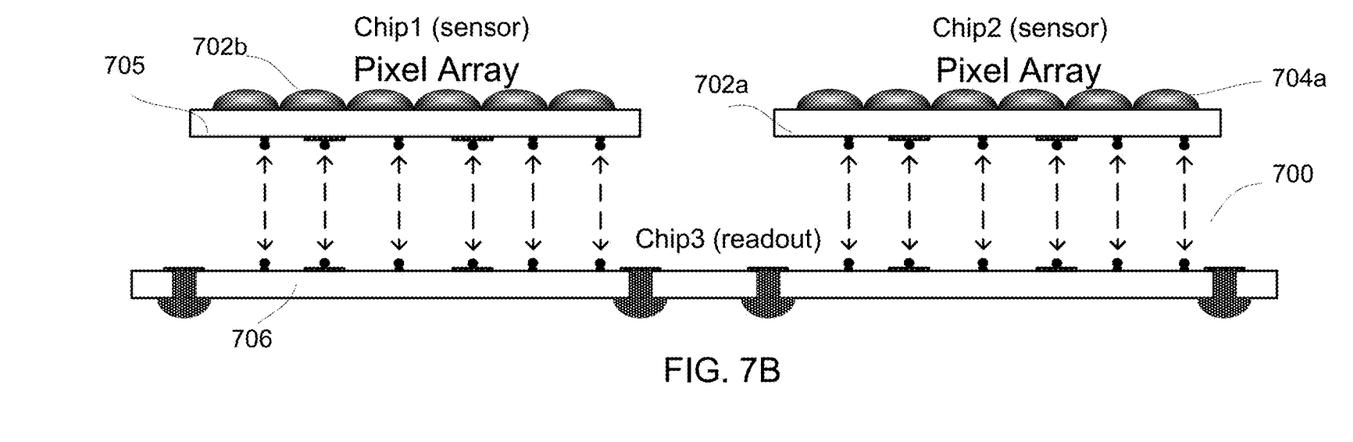

FIGS. 7A and 7B illustrate a perspective view and a side view, respectively, of an implementation of an imaging sensor 700 having a plurality of pixel arrays for producing a three dimensional image. The three dimensional image sensor may be built on a plurality of substrates and may comprise the plurality of pixel arrays and other associated circuitry, wherein a plurality of pixel columns 704a forming the first pixel array and a plurality of pixel columns 704b forming a second pixel array are located on respective substrates 702a and 702b, respectively, and a plurality of circuit columns 708a and 708b are located on a separate substrate 706. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

Additionally, the teachings and principles of the disclosure may include any and all wavelengths of electromagnetic energy, including the visible and non-visible spectrums, such as infrared (IR), ultraviolet (UV), and X-ray.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. An endoscopic system comprising:
an endoscope comprising:
an image sensor located at a distal end of the endoscope; and
a light gathering lens located at the distal end of the endoscope that is angled relative to a plane extending transversely to a longitudinal axis of the endoscope, wherein the light gathering lens is configured to gather and focus light onto the image sensor;
a trocar assembly designed to pierce through tissue comprising a cannula and an obturator insertable through the cannula, the obturator comprising a shaft with a window at the distal end of the shaft, the trocar assembly configured to be operably connected to the endoscope; and
a light refracting element that is removably attached to a lumen within the shaft of the obturator and that is angled relative to the plane extending transversely to the longitudinal axis of the endoscope, wherein the light refracting element is a prism mounted within a distal end of the obturator, proximal to the window and is configured to bend light received through the window in a direction of travel toward the light gathering lens, such that the light refracting element transmits light that is substantially perpendicular to a surface of the light gathering lens;
wherein the endoscope is operably insertable within the obturator such that when the endoscope is located within the obturator the light gathering lens of the endoscope is adjacent the light refracting element within the distal end of the obturator.

2. The endoscopic system of 1, wherein the angle of the light gathering lens is about 30 degrees relative to the plane extending transversely to the longitudinal axis of the endoscope.

3. The endoscopic system of claim 1, wherein the window comprises a transparent or translucent pointed tip positioned at a distal end of the obturator of the trocar assembly.

4. A trocar assembly comprising:
a trocar;
a cannula; and an obturator, insertable through the cannula, and designed to pierce through tissue comprising a distal end and a proximal end, wherein the obturator is configured to be operably connected to an endoscope, the obturator comprising:
   a shaft with a window at or near the distal end of the shaft;
   a light refracting element that is angled relative to a plane extending transversely to a longitudinal axis of the endoscope, wherein the light refracting element is a prism mounted within the distal end of the obturator, proximal to the window and configured to bend light received through the window toward a light gathering lens associated with the endoscope, such that the light refracting element transmits light that is substantially perpendicular to a surface the light gathering lens,
   wherein the endoscope is operably insertable within the obturator such that when the endoscope is located within the obturator the light gathering lens of the endoscope is adjacent the light refracting element within the distal end of the obturator, and
   wherein the light gathering lens is angled relative to the plane extending transversely to the longitudinal axis of the endoscope, wherein the light gathering lens is configured to gather and focus light onto an image sensor of the endoscope; and
   wherein the light refracting element is angled relative to the plane extending transversely to the longitudinal axis of the endoscope to be one or both of:
     placed into the obturator to bend the light toward the light gathering lens; and
     attached to the obturator to bend the light toward the light gathering lens.

5. The trocar assembly of claim 4, wherein the trocar assembly is configured to be used with endoscope that comprises the light gathering lens that is angled relative to the plane extending transversely to the longitudinal axis of the endoscope.

6. The trocar assembly of claim 4, wherein the angle of the light gathering lens is about 30 degrees relative to the plane extending transversely to the longitudinal axis of the endoscope.

7. The trocar assembly of claim 4, wherein the retainer comprises at least one of: a mechanical structure, an adhesive, and/or a region in a lumen defined by the obturator.

8. The trocar assembly of claim 4, wherein the window comprises a transparent or translucent pointed tip positioned at a distal end of the obturator.

\* \* \* \* \*